United States Patent [19]

Barels et al.

[11] 4,292,304
[45] Sep. 29, 1981

[54] OIL BASED DENTIFRICE

[76] Inventors: Ronald R. Barels, 14 Doral Dr., Moraga, Calif. 94566; Daniel J. Ghinazzi, 1374 Mossy Ct., Concord, Calif. 94521

[21] Appl. No.: 192,465

[22] Filed: Sep. 30, 1980

[51] Int. Cl.³ .......................... A61K 9/48; A61K 9/16; A61K 9/18; A61K 31/355
[52] U.S. Cl. ........................................ 424/37; 424/49; 424/284; 424/52
[58] Field of Search ............................ 424/37, 49–58, 424/284

[56] References Cited

U.S. PATENT DOCUMENTS

| | | | |
|---|---|---|---|
| 2,004,957 | 6/1935 | Messner | 424/38 |
| 2,031,233 | 2/1936 | Stillwell | 424/49 |
| 2,090,437 | 8/1937 | Woldman | 424/53 |
| 2,778,045 | 1/1957 | Bly et al. | 424/49 |
| 3,475,533 | 10/1969 | Mayrand | 424/57 |
| 3,992,519 | 11/1976 | Hofmann et al. | 424/52 |
| 4,005,196 | 1/1977 | Jandacek et al. | 424/284 |
| 4,069,311 | 1/1978 | Mannara | 424/52 |
| 4,196,189 | 4/1980 | Raaf et al. | 424/52 |
| 4,226,851 | 10/1980 | Sompayrac | 424/284 |

OTHER PUBLICATIONS

Machlin, Vitamin E, A Comprehensive Treatise, vol. 1 (1980), Marcel Dekker, Inc., N.Y., N.Y., pp. 580–584, 597, 619.
Ropte, Chem. Abstr. 63, #5445f (1965), Vitamin E Gelatin Capsules.
Federov et al., Chem. Abstr. 70, #10293g (1969), Prevention of Experimental Caries in Rats by the Administration of Vitamin . . . E.
Schneider et al., Chem. Abstr. 71, #36757g (1969), Effects of Vitamin E on the Formation and the Structure of Enamel and Dentin.

*Primary Examiner*—Shep K. Rose
*Attorney, Agent, or Firm*—Phillips, Moore, Weissenberger, Lempio & Majestic

[57] ABSTRACT

The present invention provides an encapsulated dentifrice comprising an edible capsule within which is contained a substantially anhydrous, oil based dentifrice composition and an abrasive agent suitable for removal of plaque. The capsule is water soluble and oil insoluble, and is particularly useful for travellers, and the like. A preferred oil based dentifrice composition includes a source of vitamin E.

2 Claims, 1 Drawing Figure

OIL BASED DENTIFRICE

BACKGROUND OF THE INVENTION

1. Field of the Invention

The present invention generally relates to an oil based dentifrice, and more particularly to an oil based dentifrice which includes a source of vitamim E and which may be encapsulated in an edible capsule.

2. Prior Art

Anhydrous toothpastes including an oil component are known. For example, U.S. Pat. No. 3,574,824, issued Apr. 13, 1971, inventors Echeandia, et al., discloses an anhydrous toothpaste having an oil component in an amount up to about 35 weight percent which may be used as a vehicle for water incompatible enzymes and the like. U.S. Pat. No. 2,089,529, issued Aug. 10, 1937, inventor Behr, discloses an anhydrous, acidic toothpaste having an oil component in an amount of about 49 weight percent.

Among the disadvantages with prior known, anhydrous toothpastes having oil components therein have been an unpleasant mouth feel when used, often interpreted as an oily sensation, and a reduced shelf life with respect to conventional, hydrous toothpastes due to the tendency of the oil component to oxidize and become rancid.

SUMMARY OF THE INVENTION

Accordingly, it is an object of the present invention to provide a dentifrice which includes an oil base resistant to oxidation, which has little or no oily sensation when utilized for oral hygiene, and which also includes sufficient of an abrasive component to assist in the removal of plaque.

It is a further object of the present invention to provide such an oil based dentifrice in an encapsulated form, the encapsulation preferably by means of an edible capsule of a size and shape suitable for consumption in one use.

These and other objects and advantages are provided in one aspect of the present invention by an oil based dentifrice with vitamin E in an amount of at least about 1 weight percent and an abrasive agent in an amount sufficient to assist in the removal of plaque.

Another aspect of the present invention is an encapsulated dentifrice comprising a water soluble, edible capsule in which is contained a quantity of a substantially anhydrous, oil based dentifrice, which preferably includes at least about 10 miligrams of vitamin E therein.

DETAILED DESCRIPTION OF THE PREFERRED EMBODIMENTS

Figure 1:
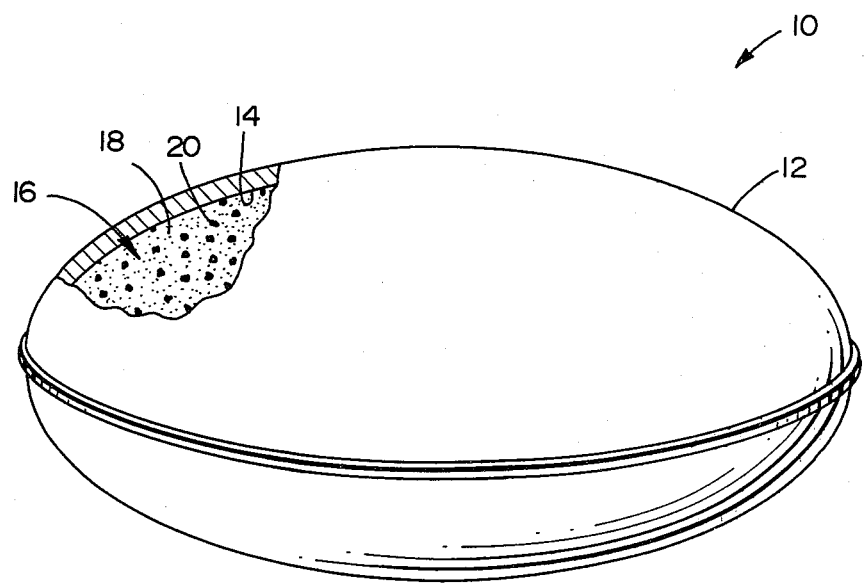
FIG. 1 is a perspective, enlarged view of an encapsulated dentifrice embodiment in accordance with the present invention.

FIG. 1 illustrates an encapsulated dentifrice embodiment 10 in accordance with the present invention which includes a capsule 12 having an interior chamber 14. An oil based dentifrice composition 16 is within interior chamber 14 and is encapsulated by capsule 12. By encapsulation is meant that capsule 12 normally contains dentifrice composition 16 without leakage therefrom until dentifrice embodiment 10 is utilized for tooth cleansing.

Capsule 12 is formed of an edible material which is substantially water soluble but is oil insoluble. A preferred material for capsule 12 is gelatin of sufficient hardness to permit the encapsulation and to resist rupture during handling, packaging, and shipping of dentifrice embodiment 10.

Capsule 12 is preferably adapted to be placed into the user's mouth and be readily crushed between the teeth to release a quantity of dentifrice composition 16 for tooth cleansing. The ruptured capsule 12 may be chewed and/or swallowed. Dentifrice composition 16 is anhydrous and thus does not leak from, or permeate, the oil insoluble capsule 12. Unlike hydrous toothpastes or gels, an oil base 18 of dentifrice composition 16 readily flows about the teeth when capsule 12 is crushed, and thus dentifrice composition 16 is easily dispersed throughout the oral cavity, with or without the aid of a toothbrush or the like. An abrasive agent 20 of dentifrice composition 16 is suspended by oil base 18, and is carried with oil base 18 into contact with tooth areas susceptible to plaque formation. Abrasive agent 20 aids in the removal, or dispersal, of plaque, particularly when dentifrice embodiment 10 is utilized in conjunction with dental floss or the like.

The preferred quantity of dentifrice composition 16 encapsulated by each capsule 12 is suitable for one oral treatment, normally from about 0.5 g to about 1 g, and this preferred quantity shall hereinafter sometimes also be referred to as a "dose". Encapsulated dentifrice embodiment 10 may be readily packaged in foil, plastic or the like, and dispensed to travellers or guests for their convenient use.

In the best mode contemplated for the present invention, the oil based dentifrice composition 16 is encapsulated by a capsule 12 and includes the oil base 18 having a sufficient quantity of a source of vitamin E so as to provide at least about 10 mg. of vitamin E per dose. However, oil based dentifrice composition 16 need not be encapsulated by edible capsule 12, but may be packaged and used in a conventional manner.

The oil base 18 is in a weight ratio with respect to the abrasive agent 20 of from about 1:8 to about 8:1, more preferably a weight ratio greater than about 1:1. Oil base 18 is at least about 10 wt.% of dentifrice composition 16, more preferably is the major component of the dentifrice composition 16, and most preferably is from about 60 weight percent to about 85 weight percent of the total composition.

The oil based dentifrice composition 16 as a composition of matter shall now be more fully described.

Oil Base

The oils which may comprise the oil base of the dentifrice composition are edible, are preferably chosen from the various vegetable oils in their natural, or unsaturated, state, and are liquid at room temperature (that is, above about 40° F.). A particularly preferred vegetable oil is safflower oil.

It has been discovered that the inclusion of a sufficient quantity of a source of vitamin E in the oil base of the dentifrice composition substantially reduces or eliminates the oily sensation, or unpleasant mouth feel, of the oil base and tends to reduce oxidation of the oil base. This is particularly important where the oil base constitutes the major component of the dentifrice composition.

It is also believed that inclusion of vitamin E in the oil base, in the presence of a quantity of abrasive agent, assists in providing beneficial oral health of the tissues adjacent a user's teeth, usually in conjunction with the removal of plaque by means such as a toothbrush, dental floss or the like. That is, it is believed that the inclusion of a sufficient source of vitamin E in the oil base is of assistance as part of an oral health program for user's with gingival irritations, and may be useful following oral surgery, or for user's with incipient gum deterioration.

A sufficient quantity of a source of vitamin E in the oil base to substantially reduce or eliminate the oily sensation, or unpleasant mouth feel, of the oil base is wherein the source of vitamin E provides at least about 1 weight percent of vitamin E with respect to the dentifrice composition. Where the dentifrice composition is encapsulated so as to include a predetermined quantity, or dose, of the dentifrice composition, then the source of vitamin E preferably provides at least about 10 mg of vitamin E. For example, where the dose is 1 g., then the weight percent of vitamin E in the dentifrice composition will be at least about 1 wt.%; whereas where the dose is 0.5 g, then the weight percent of vitamin E in the dentifrice composition will be at least about 2 wt.%.

An international unit of vitamin E is generally considered to be equal to 1 miligram of standard DL-alpha-tocopheryl acetate. Although vitamin E (also known as alpha-tocopherol) is present in very small concentration (0.1–0.3%) in wheat germ, corn, sunflower seed, rape seed, and soy bean oil, a use of such oils, by themselves, does not result in sufficient quantities fo vitamin E for providing the source of vitamin E.

Commercial, edible sources of vitamin E are available, usually as oils, in various international unit amounts. These commercially available sources of vitamin E frequently include various extender oils, usually vegetable oils, such as corn flower oil and the like. Such commercially available sources of vitamin E are suitable for use as the source of vitamin E in the oil base of the present invention, so long such commercial preparations are utilized in the formulation of the present invention so as to provide at least about 1 wt.% of vitamin E in the oil based dentifrice composition, or at least about 10 mg vitamin E per dose when encapsulated.

Abrasive Agent

The oil based dentifrice composition of the present invention further comprises an abrasive agent. The abrasive agent of the oil based dentifrice composition should be present in a sufficient amount and be of sufficient abrasiveness so as to aid in the control of plaque when the dentifrice composition is used in conjunction with a toothbrush, dental floss or the like. Where the dentifrice composition is intended for daily use, the abrasiveness should not be excessive, that is, should not abrade tooth enamel over extended periods of use.

It is believed that a sufficient quantity of abrasive agent may be as little as 3 weight percent of the dentifrice's total weight, because of an abrasive-enhancing effect of the abrasive agent in the presence of the oil base. A more preferred quantity of the abrasive agent in the oil based dentifrice composition is from about 5 weight percent to about 35 weight percent with respect to the total composition weight. Larger amounts of the abrasive agent, particularly wherein the amount of abrasive agent exceeds a weight ratio with respect to the oil base of about 1:1, may tend to result in excessive abrasion, or lead to settling out of the abrasive agent, which is normally and desirably suspended in the oil based dentifrice composition.

Sufficient abrasion for daily use is wherein the abrasive agent has a radioactive dentine abrasion value of from about 100 to about 500. Suitable abrasive agents include, for example, calcium carbonate, dicalcium phosphate, calcium pyrophosphate, calcium sulphate, sodium metaphosphate, aluminum silicate, silica xerogels, and silica hydrogels.

The oil based dentifrice composition is preferably anhydrous, and must be anhydrous when encapsulated by capsule 12 of the dentifrice embodiment 10. Several of such compounds suitable as abrasive agents in the present invention are available in both anhydrous as well as hydrous forms. The hydrous forms are where the water is bound. Although several of these compounds may thus contain bound water, which can usually be driven off by the application of sufficient heat, this water is normally not freely available in the composition. Accordingly, such bound water forms of abrasive agents are suitable for inclusion in the oil base and thus encapsulation by capsule 12.

Surfactant Agent

It is desirable that the oil based dentifrice composition include a surfactant agent as a component thereof. The surfactant component functions as a foaming or sudsing agent for the composition when exposed to water, or saliva, in the mouth during use. A variety of conventionally known surfactant agents, including non-ionic, cationic and anionic surfactants, for use in the oral cavity are suitable for inclusion into the dentifrice composition. For example, cetyl pyridinium fluoride, bis-2-hydroxyethylalkylamineoxide, sodium lauryl sulfate, and fatty acid esters of sodium isethionate, are suitable as the surfactant component. Various naturally derived compounds having foaming properties, such as the saponins, are also suitable as the surfactant agent. Sodium lauryl sulfate (SLS) is a preferred surfactant agent, either by itself or as a mixture with another surfactant. A mixture of SLS and another surfactant is particularly preferred, as the foaming and sudsing functions of SLS, by itself, tend to be inhibited by the oil base. The amount of surfactant agent for inclusion into the oil based dentifrice composition is preferably an amount in the range of from about 3 weight percent to about 15 weight percent of the total composition.

Other Components

The oil based dentifrice composition may include oral health agents, particularly of the fluoride type, for example sodium fluoride, lithium fluoride, stannous fluoride, potassium fluoride, ammonium fluoride, sodium fluorstanide, stannous chlorofluoride, or sodium monofluorophosphate. Stannous fluoride is a particularly preferred source of fluoride.

Additional components such as sweetners and flavoring oils may also be incorporated into the oil based dentifrice composition, for example saccharin, peppermint oil, spearmint oil, clove oil and the like. The quantity of a sweetening component such as saccharin will normally be quite small, as saccharin has a relatively low solubility in the oil base.

Examples

Ten oil based dentifrice compositions in accordance with the present invention were prepared and are illustrated by Table I, below.

TABLE I

| Composition 1 | | |
|---|---|---|
| Component | Wt. % | |
| Vit. E oil (13.5 I.U./cc) | 80.6 | (1.3 of vit. E) |
| Hydrous silica gel* | 7.0 | |
| $C_9H_{19}\phi$-$O(CH_2CH_2O)N-CH_2OH$ | 8.0 | |
| Sodium lauryl sulfate | 3.0 | |
| Stannous fluoride | 0.4 | |
| Saccharin/flavoring oil | 1.0 | |

| Composition 2 | | |
|---|---|---|
| Component | Wt. % | |
| Vit. E oil (118.4 I.U./cc) | 75.5 | (10.6 of vit. E) |
| Hydrous silica gel* | 15.0 | |
| Myristic acid - 2-sulfoethyl ester | 6.0 | |
| Sodium lauryl sulfate | 2.0 | |
| Stannous fluoride | 0.3 | |
| Saccharin/flavoring oil | 1.2 | |

| Composition 3 | | |
|---|---|---|
| Component | Wt. % | |
| Vit. E. oil (13.5 I.U./cc) | 77.5 | (1.2 of vit. E) |
| Hydrous silica gel* | 12.0 | |
| Monocarboxyl Coco imidazoline | 6.0 | |
| Sodium lauryl sulfate | 1.0 | |
| Stannous fluoride | 0.3 | |
| Saccharin/flavoring oil/colorant | 2.8 | |

| Composition 4 | | |
|---|---|---|
| Component | Wt. % | |
| Vit. E oil (13.5 I.U./cc) | 62.6 | (1.0 of vit. E) |
| Hydrous silica gel* | 25.0 | |
| Coconut acid ester of sodium isethionate | 9.5 | |
| Stannous fluoride | 0.4 | |
| Saccharin/flavoring oil/colorant | 2.6 | |

| Composition 5 | | |
|---|---|---|
| Component | Wt. % | |
| Safflower oil | 70.0 | |
| Vit. E. oil (126.8 I.U./cc) | 8.6 | (1.3 of vit. E) |
| Hydrous silica gel** | 11.8 | |
| Myristic acid-2-sulfoethyl ester, sodium salt | 5.7 | |
| Sodium lauryl sulfate | 2.7 | |
| Stannous fluoride | 0.3 | |
| Saccharin/flavoring oil | 1.0 | |

| Composition 6 | | |
|---|---|---|
| Component | Wt. % | |
| Vit. E. oil (13.5 I.U./cc) | 78.6 | (1.3 of vit. E) |
| Silica aerogel*** | 11.8 | |
| Myristic acid-2-sulfoethyl ester, sodium salt | 5.7 | |
| Sodium lauryl sulfate | 2.7 | |
| Sodium fluoride | 0.3 | |
| Saccharin/flavoring oil | 1.0 | |

| Composition 7 | | |
|---|---|---|
| Component | Wt. % | |
| Vit. E. oil (25.4 I.U./cc) | 42.0 | (1.3 vit. E) |
| Hydrous Silica Gel | 10.0 | |
| Silica Xerogel | 9.4 | |
| Silica Aerogel | 25.2 | |
| Myristic Acid-2 sulfoethyl ester, sodium salt | 8.3 | |
| Sodium lauryl sulfate | 2.2 | |
| Sodium fluoride | 0.4 | |
| Saccharin/Flavoring oil | 2.5 | |

| Composition 8 | | |
|---|---|---|
| Component | Wt. % | |
| Hydrous Silica Gel | 11.8 | |
| Silica Xerogel | 3.2 | |
| Silica Aerogel | 49.4 | |
| Vit. E. oil (42.3 I.U./cc) | 25.0 | (1.2 vit. E) |
| Myristic Acid-2 sulfoethyl ester, sodium salt | 6.4 | |
| Sodium lauryl sulfate | 1.9 | |
| Sodium fluoride | 0.3 | |
| Saccharin/Flavoring oil | 2.0 | |

| Composition 9 | | |
|---|---|---|
| Component | Wt. % | |
| Hydrous silica gel | 15.5 | |
| Silica Xerogel | — | |
| Silica Aerogel | 63.8 | |
| Vit. E. oil (109.9 I.U./cc) | 9.9 | (1.3 vit. E) |
| Coconut fatty acid-2 sulfoethyl ester sodium salt | 8.0 | |
| Sodium lauryl sulfate | 1.0 | |
| Sodium fluoride | 0.3 | |
| Saccharin/Flavoring oil | 1.5 | |

| Composition 10 | | |
|---|---|---|
| Component | Wt. % | |
| Vit. E. oil (13.5 I.U./cc) | 80.9 | (1.3 vit. E) |
| Silica Xerogel | 8.5 | |
| Myristic acid-2 sulfoethyl ester, sodium salt | 7.0 | |
| Sodium lauryl sulfate | 1.5 | |
| Sodium fluoride | 0.3 | |
| Saccharin/Flavoring oil | 1.8 | |

*Total bound water = 31%, RDA = 500, particle size about 12 micron
**Total bound water = 45%, RDA = 500, particle size about 11 micron
***Particle size about 3 micron All of the compositions illustrated by Table I, above, provided an oil based dentifrice composition with little or no oily sensation in the mouth. Each was readily dispersed in the user's mouth, and displayed an excellent debriding action upon food material between the teeth and upon plaque in conjunction with routine flossing and/brushing. Compositions 1–6 and 10 displayed excellent suspension of the abrasive agent in the oil base. The abrasive component of compositions 7, 8 and 9 however, tended to settle out from suspension in the oil base due to the relatively larger amount of abrasive agent and relatively lower amount of oil.

A first composition substantially equivalent to composition 2, above, was formulated and encapsulated by 1 gram doses into gelatin capsules (so as to provide about 106 mg vitamin E/dose). A second composition, substantially equivalent to composition 4, above, was formulated and encapsulated by 1 gram doses into gelatin capsules (so as to provide about 10 mg vitamin E/dose). A control composition analogous to composition 4, above, but wherein safflower oil entirely replaced the vitamin E oil, was formulated and encapsulated by 1 gram quantities into gelatin capsules (so as to provide substantially no vitamin E/dose). These three compositions were then utilized by thirty dental patients having mild gingival irritations as follows.

A first group of ten patients was instructed to brush twice daily (morning and evening) with a dose at each brushing, the doses having the first composition therein, and to floss once daily. A second group of ten patients was given identical instructions, but these patients were brushing with the second composition. A third group of ten patients was likewise given identical instructions, but these patients were brushing with the control composition. (None of the patients knew the identity of the formulations). After thirty days, all thirty patients were examined. The gums of 29 patients were found to have improved, with the first group having the most improvement, followed by the second group, and the least improvement displayed by the control group. One patient (from the second group) showed little or no improvement which was believed due to extremely poor overall oral hygiene and to not having followed directions. The modest, but general, improvement of the control group may be due to a placebo effect, and/or to generally better oral hygiene during the test period.

Preparation of dentifrice compositions in accordance with the present invention may be where the components are simply admixed. The abrasive agent 20 is readily suspended in oil base 18 when the weight ratio of abrasive agent to oil base is not greater than about 1:1. Thereafter, the dentifrice composition may be encapsulated by edible capsule 12, for example by various conventional encapsulating means, to form the dentifrice embodiment 10.

In summary, the preferred dentifrice composition, which includes a source of vitamin E in the presence of an abrasive agent, results in a unique product for oral health care. Further, dentifrice embodiment 10 provides a particularly convenient, easily dispensed article for use by travellers or the like.

We claim:
1. An encapsulated dentifrice comprising:
   an edible capsule having an interior chamber, said capsule adapted to be placed into a user's mouth, readily crushed between the teeth to release a dentifrice, and then the ruptured capsule chewed and/or swallowed, said capsule being formed of a gelatin material which is water soluble and which is substantially oil insoluble;
   a quantity of from about 0.5 g to about 1 g of a substantially anhydrous, oil based dentifrice within said interior chamber and encapsulated by said capsule, said dentifrice including an edible oil base in an amount of from about 10 weight percent to about 85 weight percent of said dentifrice to thereby easily disperse said dentifrice throughout the oral cavity, an abrasive agent in an amount of from about 3 weight percent to about 35 weight percent of said dentifrice suspended therein to aid in the disposal of plaque, a surfactant agent, and at least about 10 mg of vitamin E.
2. The encapsulated dentifrice as in claim 1 wherein said capsule further contains a fluoride agent.

* * * * *